United States Patent [19]

Hoebel

[11] 4,236,086

[45] Nov. 25, 1980

[54] APPARATUS FOR THE DETECTION AND PROCESSING OF ELECTRIC SIGNALS

[75] Inventor: Peter Hoebel, Erlangen, Fed. Rep. of Germany

[73] Assignee: Siemens Aktiengesellschaft, Berlin & Munich, Fed. Rep. of Germany

[21] Appl. No.: 953,189

[22] Filed: Oct. 20, 1978

[30] Foreign Application Priority Data

Nov. 25, 1977 [DE] Fed. Rep. of Germany ....... 2752783

[51] Int. Cl.³ .............................................. H02J 3/00
[52] U.S. Cl. .................................... 307/149; 250/551; 336/DIG. 2; 307/326
[58] Field of Search ................. 307/149, 17, 323–326, 307/112, 116, 150–157; 128/303.13–303.19; 336/DIG. 2; 361/142, 179; 250/551

[56] References Cited

U.S. PATENT DOCUMENTS

| | | | |
|---|---|---|---|
| 3,387,606 | 6/1968 | Crafts et al. | 336/DIG. 2 X |
| 3,549,990 | 12/1970 | Hochheiser | 336/DIG. 2 X |
| 3,743,989 | 7/1973 | Nicolas et al. | 336/DIG. 2 X |
| 3,792,284 | 2/1974 | Kaelin | 250/551 |
| 3,913,001 | 10/1975 | Kayama | 250/551 X |
| 4,045,120 | 8/1977 | de Corlieu et al. | 250/551 X |

FOREIGN PATENT DOCUMENTS

| | | |
|---|---|---|
| 1220920 | 7/1966 | Fed. Rep. of Germany . |
| 279993 | 11/1927 | United Kingdom . |
| 1025448 | 4/1966 | United Kingdom . |
| 1080658 | 8/1967 | United Kingdom . |
| 1366134 | 9/1974 | United Kingdom . |
| 1383577 | 2/1975 | United Kingdom . |
| 1398166 | 6/1975 | United Kingdom . |
| 1447469 | 8/1976 | United Kingdom . |
| 1456394 | 11/1976 | United Kingdom . |
| 1493992 | 12/1977 | United Kingdom . |
| 1503979 | 3/1978 | United Kingdom . |
| 1527014 | 10/1978 | United Kingdom . |

OTHER PUBLICATIONS

*Electronics*, Sep. 1, 1969, p. 38, "Medical Electronics".

*Primary Examiner*—John Gonzales
*Assistant Examiner*—W. J. Brady
*Attorney, Agent, or Firm*—Hill, Van Santen, Steadman, Chiara & Simpson

[57] ABSTRACT

In the exemplary disclosure, a signal transmitter and a signal processing part, which are interconnectable in the signal path by means of a contact plug, have a galvanically separative coupling location in the signal path with primary and secondary coupling members. The object is to design a plug-in connection that demonstrates a particularly good insulation effect. This is achieved in that of any given two inter-associated primary and secondary coupling members one of the two coupling members is disposed in the contact plug part on the side of the signal processing part and the other is disposed in the corresponding plug-in contact part of the signal transmitter so that upon establishment of the plug contact between the signal transmitter and the signal processing part the coupling members join together in spatial proximity as primary and secondary coupling members to form a coupling location.

10 Claims, 4 Drawing Figures

APPARATUS FOR THE DETECTION AND PROCESSING OF ELECTRIC SIGNALS

BACKGROUND OF THE INVENTION

The invention relates to an apparatus for the detection and processing of electric signals, consisting of a signal transmitter and a signal processing part, which are interconnectable in the signal path by means of a contact plug; and providing a galvanically separative coupling location in the signal path with primary and secondary coupling members.

Particularly in medical technology, it is common practice when tapping bio-signals to galvanically isolate the signal electrodes from the processing part by means of a coupling location. Thereby, an occurrence of possibly dangerously high leakage currents is to be prevented from the outset. An apparatus of this type with such a coupling location is known, for example, from the GB-LP No. 13 98 166. In this apparatus, the actual coupling location, which uses inductive (magnetic) transformers for the transmission of the actual use signal as well as for the energy transmission, is located outside of the actual processing apparatus in the line connection between the electrodes and the apparatus. In order to be put into operation, this coupling location as a complete component must first be plugged into the actual processing apparatus. This plug-type connection for the coupling location as a complete component also including the connection of the electrodes to the coupling location is, however, unsatisfactory, since, because of the very short air gap and leakage distances which are unavoidable in the desired compact design, the respective contact connection can hardly be insulated in terms of high voltage in the manner demanded by safety factors. The same also applies, however, to a heart-signal monitoring or processing apparatus as it is described in the periodical Electronics, Sept. 1, 1969, page 38. In this apparatus, the coupling location (again with inductive coupling for the transmission of use signal and energy) is, indeed, located in a common apparatus housing with the processing part. The actual EKG acceptance electrodes are then, however, connected directly through the apparatus housing to the coupling location, which then, therefore, gives rise to insulating problems at this passage through the housing.

SUMMARY OF THE INVENTION

The object of the present invention is to eliminate this disadvantage of the known apparatus, i.e. to create a plug-in connection that demonstrates a particularly good insulation effect from the very outset.

The object is inventively achieved, in that of two respective primary and secondary coupling members associated with one another, one of the two coupling members is provided in the contact plug part at the side of the signal processing part and the other of the two coupling members is provided in the corresponding plug-in contact part of the signal transmitter, so that upon establishment of the plug contact between the signal transmitter and the signal processing part both coupling members join together in spatial proximity as primary and secondary coupling members to form a coupling location.

In the apparatus according to the invention with the inventive coupling location, equalizing currents, even those that arise particularly upon application of a high voltage load, no longer flow between two contact locations lying close to one another; rather, at least one of the contact locations enters into the plug-in connection as a contact plug whose surface area can be designed as large as desired. This also, as desired, results in air gap and leakage distances of any desired length for possibly flowing leakage currents. The electric strength increases by a multiple and insulation problems no longer occur.

In an advantageous embodiment of the invention, the coupling member on the side of the signal source in the direction of the signal transmission is to assume the primary function and the coupling member on the side of the signal processing part is to assume the secondary function. The result then is, for example in the case of the transmission of physiological signals from a signal tap to the signal processing part in the actual apparatus, that the primary coupling member is then in the contact plug on the side of the electrode and the secondary member for the signal transmission is then in the contact plug part on the side of the processing apparatus. If, however, marker signals such as calibration pulses or signals are to be transmitted from the side of the processing apparatus in the direction of the contact connection or electrodes, then, because of the directional reversal, in the coupling location a coupling member on the side of the processing apparatus assumes the primary function and a coupling member on the side of the transmitter plug-in contact assumes the secondary function. In a further advantageous embodiment, the coupling location is to be divided into primary and secondary coupling members for use signal transmission and into further primary and secondary coupling members for the energy transmission for the power supply.

Further advantages and details of the invention derive from the description of two sample embodiments on the basis of the accompanying sheets of drawings in conjunction with the subclaims; and other objects, features and advantages will be apparent from this detailed disclosure and from the appended claims.

BRIEF DESCRIPTION OF THE DRAWINGS

FIG. 1 comprising FIG. 2 comprising

DETAILED DESCRIPTION

Figure 1A:
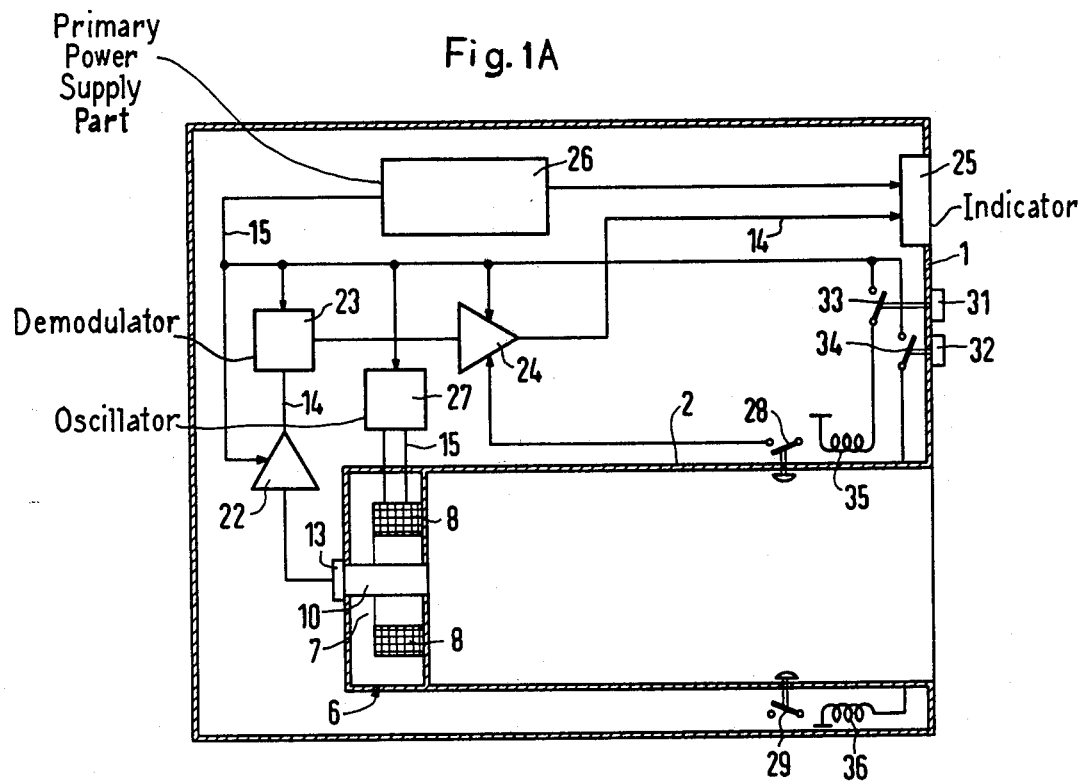
FIGS. 1A and 1B shows a sample embodiment of the invention, in which the plugging together of primary and secondary coupling members ensues in a longitudinal coupling process.
Figure 1B:
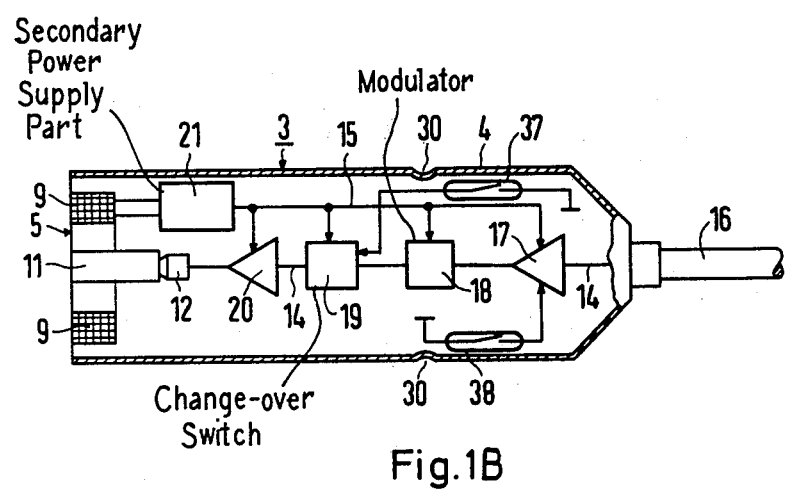

An apparatus housing 1 of for example sheet metal is illustrated in longitudinal section in FIG. 1A. The apparatus housing 1 exhibits a preferably cylindrical indentation or contact plug recess 2 that is fabricated of non-magnetic but electrically conductive material. Aluminum can serve as the material for the wall of the recess, designed for example as a cylinder. The recess 2 represents a contact plug part on the apparatus side. The corresponding counter contact part 3 is illustrated below in FIG. 1B, also in longitudinal section. This counter contact part consists of an elongated casing (also cylindrical when recess 2 is cylindrical) with a casing 4 of insulating material of high electric strength. As insulating material, a synthetic plastic with inner metallization enters into consideration. The inner metallization serves particularly for high frequency shielding.

The end-face 5 of the counter contact part 3 consists of a translucent synthetic, for example Plexiglas.

The contact plug part 2 has an installation space 7 at the end 6 that lies inside the apparatus. In this installation space there is a coil 8 (preferably annular) serving, in the case in question, as the primary coupling element for energy transmission into the casing 3 of the counter plug-in contact. As secondary coupling member, the plug-in member 3 accordingly comprises a secondary coil 9 (also preferably annular) at or near the end-face 5 of the contact plug 3.

An opto-coupler serves for the actual use signal transmission, particularly for the transmission of EKG signals. This opto-coupler exhibits an initial fiber optic light guide part element 10, which is provided in the installation space 7 of the contact recess 2, as illustrated in FIG. 1A. In the case of a use signal transmission from the counter contact part 3, this glass-optic light guide port element 10 assumes the secondary function. A corresponding cooperating joining port 11 in the plug-in part 3 serves for the primary transmission. The incident light radiation into the primary joining piece 11 ensues by means of light-emitting diode 12. Correspondingly, the glass-optic light guide port 10 in the apparatus housing 1 comprises a photo receiver 13 (for example, a silicon diode).

In the manner illustrated in FIG. 1, thus, the coils 8 or 9 respectively as well as the glass-optic light guide ports 10 or 11 respectively with accompanying light source 12 and light receiver 13 are individual components (primary and secondary coupling members respectively) of a coupling location for the galvanically separated transmission of use signals and power supply. These individual components of a coupling location, however, only become active as a coupling location in close spatial proximity at the moment of plugging together, i.e. the moment of plugging the contact part 3 into the contact receiving part 2.

Only in this case, i.e. in a plugged-in condition, is there, thus, a common signal path 14 for the use signals and only then is there a closed energy path 15 for the power supply. With regard to the use signal supply, this means that for example EKG signals are tapped from the patient via an EKG electrode (not, though, illustrated) attached to the cable connection 16 and transmitted via the signal line 14 to a preamplifier 17 in the contact plug part, FIG. 1B. From here, the amplified signals are then transmitted to a driver stage 20 after modulation in a modulator 18 (preferably a frequency or pulse duration modulator) and, if necessary, after influencing in a switching member 19. From the driver stage 20, the light-emitting diode 12 is then directly subjected to the modulated signals. The power supply in the plug contact part 3 is assumed by the secondary power supply part 21, which is connected to the secondary coil 9 for energy transmission.

In the apparatus itself, FIG. 1A, the optosignals are transmitted to the preamplifier 22 after conversion into electrical signals in the optoreceiver 13 and are supplied from this preamplifier to a demodulator 23 for demodulation. From this they are then fed to an indicator 25, after further amplification and filtering, if necessary, in an output amplifier 24. The indicator 25 must be taken in its broadest meaning, i.e. it can be a registering recorder or oscilloscope or, for example, only a simple digital or analog indicator instrument.

The primary power supply part 26 serves for the primary energy supply in the apparatus 1 and can be a power pack with appropriate exterior connection to the external power network; it can, however, also be a question of a simple battery supply. The energy transmission to supply the primary coil 8 proceeds by means of an oscillator 27. Beyond this, in FIG. 1A, the plug connection 2 of the apparatus exhibits two microswitches 28, 29 that can be switched from a groove 30, FIG. 1B, in the counter contact part 3. The switching operation, however, is only triggered, when in the interconnected state the groove 30 of the plug-in part 3 is situated at the microswitches 28, 29 in the contact plug part 2. By providing various grooves at various distances from the end faces 5, various plug-in contact parts 3 can be variously marked. In so doing, for example, switching operations can be triggered dependent upon the type of the plug-in contact parts 3. Plug connections with switching contacts on the basis of grooves per se are previously known independent of the present invention, for example from the German Auslegeschrift No. 12 20 920.

Beyond this, e.g., two press buttons 31, 32, FIG. 1A, are also provided on the front side of the apparatus housing 1, which when actuated can excite coils 35 and 36 respectively via switches 33, 34. Thereby, reed switches 37 or 38, FIG. 1B, in the counter contact part 3 are actuated. By actuating reed switches 37 or 38, change-over operations can be triggered at change-over switch 19 or at amplifier 17 respectively, for example such that change-over is accomplished upon insertion of markers or tuning-in of various amplification stages.

The reed switches 37 or 38 respectively constitute, together with their excitation coils 35 or 36 respectively, a further complement of the complete coupling location by means of two further paired individual coupling members assigned to each other.

In FIG. 2, a modification of the sample embodiment according to FIG. 1 is illustrated, to the effect that the plugging together no longer ensues in a longitudinal coupling process but in a lateral coupling process. In this case, for example, the plug recess 2' and counter (cooperating) contact plug 3' are thus developed rectangularly. The transition surfaces for the secondary coupling coil 9 and the primary glass-optic light guide port element 11 are no longer arranged at the end face 39 of the contact plug 3'. They are now arranged on the side face at a translucent window 40 perpendicular to the arrangement of FIG. 1.

As a further possible modification, the sample embodiment of FIG. 2 further exhibits a color code identification field 41 and/or magnetic identification field 42. This identification code, together with suitable cooperating scanners on the processing apparatus side, can trigger switching processes or also amplifier switch-overs corresponding to those of the identification groove of the sample embodiment of FIG. 1.

Figure 2A:
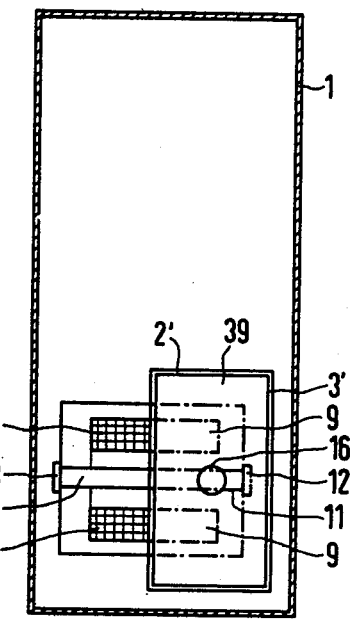
FIGS. 2A and 2B shows a sample embodiment of the invention, in which the plugging together ensues in a lateral coupling process.
Figure 2B:
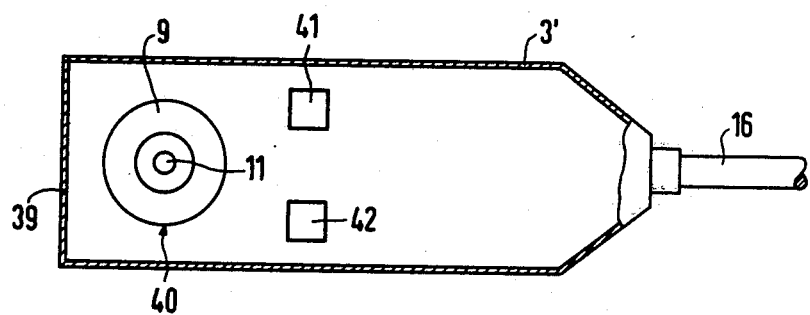

FIG. 2A shows the apparatus 1 and the signal source contact plug 3' in the plugged-in state. In FIG. 2B, the contact plug 3' is illustrated by itself in longitudinal section.

In the sample embodiments of both FIGS. 1 and 2 the apparatus housing 1 is at ground potential (that is to say at the potential of a grounded conductor). The potential of the casing of the contact plug 3', on the other hand, floats freely. It is now, however, immediately apparent, that leakage currents between the casing and the contact plug are offered air gap and leakage paths of any desired length, on the basis of the wholly special inventive contacting. In this way, the desired high electric strength with a minimum of insulation problems is also effected.

The sample embodiments refer to an apparatus specifically for medical application, i.e. particularly for the transmission of physiological signals such as EKG, blood pressure, temperature, etc. from the patient to a processing apparatus. The invention, however, is in no case restricted to purely medical application. It can also, of course, be universally employed in general measurement techniques. A particular field of application can, withal, be general read-out transmission, where for example read-outs are transmitted between two computers and coupling locations must be built into the transmission lines for the purpose of supressing equalizing (compensating) currents because of interference influences.

It will be apparent that many modifications and variations may be effected without departing from the scope of the novel concepts and teachings of the present invention.

I claim as my invention:

1. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8; 10) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, the coupling location of the contact plug means having associated therewith at a common interface (5, 40) primary and secondary coupling members (10; 11) for a use signal transmission and further primary and secondary coupling members (8; 9) providing energy transmission for power supply coupling, characterized in that, as primary and secondary coupling members for the use signal transmission, fiber optic light guide port elements (11; 10) are provided, of which a first port element (10) is disposed in the contact plug part (2, 2') on the side of the signal processing part (1) and the other fiber optic light guide port element (11) is located in the corresponding plug-in contact part (3, 3') of the signal transmitter (16), so that in the plugged-in state the fiber optic light guide port elements of the one and the other side are positioned relative to one another to provide an essentially continuous (seamless) signal transmission path.

2. Apparatus according to claim 1, characterized in that two fiber optic light guide port elements (10, 11) are flatwise joinable to one another at confronting endfaces upon plugging-in of the contact plug means.

3. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8; 10) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, wherein, for the transmission of signals from a signal source to a processing apparatus, the processing apparatus housing (1) exhibits a recess (2, 2'), which represents a contact plug part on the signal processing side into which the plug-in contact part (3, 3') fits, which plug-in contact part is connected via a cable (16) to the signal source, and characterized in that the contact plug recess (2, 2') forming the contact plug part in the apparatus housing (1) exhibits an installation space (7) at the end (6) that lies inside the apparatus, a coil (8) as the primary coupling element for energy transmission and a secondary glass-optic light guide port element (10) being provided in said installation space (7).

4. Apparatus according to claim 3, characterized in that in the plug-in part (3, 3') cooperating with the contact plug recess (2, 2') in the apparatus housing (1) a secondary coil (9) for the energy transmission and a second glass-optic light guide port element (11) for the use signal transmission are provided selectively: at or near the end face (5) in the case of longitudinal coupling, and at a side face in the case of lateral coupling.

5. Apparatus according to claim 3, characterized in that the contact plug recess (2, 2') in the apparatus housing (1) is fabricated of non-magnetic but electrically conductive material.

6. Apparatus according to claim 3, characterized in that the plug-in contact part (3, 3') comprises an elongated housing with a casing (4) of insulating material of high electric strength; and in that the plug-in contact part (3) has a transmission location (5, 40) formed on a translucent synthetic material.

7. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8, 10) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, wherein at least one preamplifier (17) with a use signal modulator (18) are provided in the signal path (14) in a casing of the plug-in contact part (3, 3') of the signal transmitter (16), characterized in that, in the casing, in addition to the preamplifier (17) and the modulator (18) a driver stage (20) for the operation of a light-emitting diode (12) is also provided.

8. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8; 10) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, wherein at least one preamplifier (17) with a use signal modulator (18) are provided in the signal path (14) in a casing of the plug-in contact part (3, 3') of the signal transmitter (16), characterized in that, additionally, a switch-over member (19) for triggering specific switch-over operations in signal processing members is also provided in the casing of the plug-in contact part (3, 3') of the signal transmitter.

9. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8; 10) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, wherein at least one preamplifier (17) with a use signal modulator (18) are provided in the signal path (14) in a casing of the plug-in contact part (3, 3') of the signal transmitter (16), characterized in that the plug-in contact part (3, 3') of the signal transmitter (16) includes a secondary power supply part (21) connected to a secondary coupling member (9) for the purpose of secondary power supply.

10. Apparatus for the detection and processing of electric signals, comprising a signal transmitter part and a signal processing part, primary and secondary coupling members providing signal path interconnection of said signal transmitter part and said signal processing part, and comprising a galvanically separative coupling location in the signal path interconnection between said primary and secondary coupling members, detachably interengageable contact plug means adjoining each other at the galvanically separative coupling location and comprising a contact plug part (2, 2') on the side of the signal processing part (1) and a plug-in contact part (3, 3') on the side of the signal transmitter part (16), each pair of interconnected primary and secondary coupling members (8, 9; 10, 11) of the contact plug means having one of the pair of interconnected coupling members (8; 19) disposed in the contact plug part (2, 2') on the side of the signal processing part (1) and having the other of the pair of interconnected coupling members (9; 11) disposed in the corresponding plug-in contact part (3, 3') of the signal transmitter part (16) so that upon establishment of the signal path interconnection between the signal transmitter part (16) and the signal processing part (1) each pair of coupling members (8, 9; 10, 11) join together in spatial proximity as primary and secondary coupling members to form a galvanically separative coupling therebetween at the galvanically separative coupling location, characterized in that identification fields (30; 41 or 42) are provided in or on the plug-in contact part (3, 3') of the signal transmitter (16), to which sensing contacts (e.g. 28, 29) for triggering presettable switching or operating processes are assigned in the contact plug part (2, 2') on the side of the signal processing part (1).

* * * * *